United States Patent [19]
Hoffman et al.

[11] Patent Number: 5,551,447
[45] Date of Patent: Sep. 3, 1996

[54] RESTRAINT BELT

[76] Inventors: Andrew T. Hoffman, 1020 Jamacha Rd., El Cajon, Calif. 92019; Christopher J. Hoffman, 11591 Polaris Dr., San Diego, Calif. 92126; Tracy D. Webster, 3518 Rancho Diego Cir., El Cajon, Calif. 92019; John D. Arnold, 16064 Loose Creek Rd., Jamul, Calif. 91935

[21] Appl. No.: 361,115

[22] Filed: Dec. 2, 1994

[51] Int. Cl.⁶ .............................. A61B 19/00; A61F 5/37; E05B 75/00
[52] U.S. Cl. .............................. 128/869; 128/876; 70/16
[58] Field of Search ............................ 128/869–876; 24/170, 171; 119/96; 70/14, 15, 16

[56] References Cited

U.S. PATENT DOCUMENTS

| | | | |
|---|---|---|---|
| 794,457 | 7/1905 | Gaiter | 128/876 |
| 2,324,183 | 7/1943 | Wilson | 70/16 |
| 3,013,317 | 12/1961 | Weber | 24/170 |
| 3,341,250 | 9/1967 | Rasmussen | 24/170 |
| 4,860,560 | 8/1989 | Lurdelius | 128/876 |
| 4,949,679 | 8/1990 | Wolfer | 70/16 |
| 5,031,639 | 7/1991 | Wolfer | 128/875 |
| 5,377,510 | 1/1995 | Smith | 70/16 |

OTHER PUBLICATIONS

Anon., "SDPD Eyes New Max Restraint System," *Law Enforcement Quarterly* (Feb.–Apr., 1993), pp. 25–26.

*Primary Examiner*—Michael A. Brown
*Attorney, Agent, or Firm*—Brown, Martin, Haller & McClain

[57] ABSTRACT

A restraint device and lockable buckles therefore are disclosed which serve to secure a person's arms and legs, while providing for a limited amount of movement but only under complete control of an escorting person. The device includes an elongated belt having a hasp/belt buckle connection to secure the belt around the person's waist, arm restraints each including a tether and a handcuff, each arm restraint independently attached to the belt by a tether buckle, and optionally an adjustable leg tether with buckles for restraint of one or both legs. The buckles (and handcuffs) all have locks to control releasability of each restraint or tether, with the locks all preferably operable by a single key such as a handcuff key. Use of the tethers permits the person's arms or legs to independently have limited freedom for walking, fingerprinting, holding objects, etc., while remaining under the control of the escort. The length of the belt is adjustable, so that different waist sizes can be accommodated. The device is advantageously used by law enforcement agencies, by prisons or jails, by park or forest rangers or wardens, in courts by bailiffs and by other similar agencies for restraint of violent, uncooperative or dangerous criminals. It will also find use in medical and psychiatric hospitals and facilities, particularly in emergency facilities where restraint of violent persons for appropriate emergency medical treatment may be necessary.

33 Claims, 4 Drawing Sheets

FIG. 11    FIG. 12

RESTRAINT BELT

BACKGROUND OF THE INVENTION

1. Field of the Invention

The invention herein relates to devices to restrain persons so as to restrict their ability to harm themselves or others and to aid law enforcement control of law violators. More particularly, it relates to belts and belt-like devices which are worn by the person who is to be restrained.

2. Description of the Prior Art

There are numerous instances where a person who has been acting violently, has committed violent or criminal acts or is potentially dangerous must be restrained for control or to prevent him from harming himself or those around him. (For brevity herein the description of the invention will usually refer to persons as male, but it will be understood that the invention is equally applicable to female persons.) Currently there are commercial devices such as handcuffs and arm and leg shackles which are used to provide some degree of restraint.

For instance, when a violent or potentially violent criminal is taken into custody by police officers, the officers normally secure and restrain the criminal's hands with handcuffs, so that he will not endanger the officers or other people in the immediate vicinity, such as by striking out at them or obtaining a weapon with which to assault them. Similarly, there are also many times when a prisoner must be transported from one detention facility to another or to a court, and he must be restrained against possible escape or assault. There are also situations where a mentally ill person has the potential to become violent toward others, or, equally importantly, toward himself, perhaps causing himself serious self-inflicted injuries. Another common situation occurs when persons are engaged in civil disobedience and must be removed by law enforcement officers from locations where they are demonstrating; such people often refuse to cooperate with the officers and must be physically carried from the scene, which must be done without injury to them.

Commonly in such situations the person can be initially restrained with such devices as handcuffs, leg irons, waist chains with handcuffs attached, or the like. These types of restraints are normally quite effective for their intended but limited purposes.

However, in many instances a person must not only be restrained initially but must still be able to move his arms or legs with some degree of freedom. For instance, criminals taken into custody must be able to move their arms and hands to be fingerprinted or to receive medication or give blood samples, and prisoners being transported to court or detention facilities usually need to carry items such as personal possessions and court papers with them. In such cases the person restrained must also be able to walk, if only slowly, to facilitate his movements from location to location while in custody or at court. Similarly, restrained mental patients must be able to move their arms enough to receive tranquilizing medication. The conventional restraint devices, such as handcuffs and wrist and leg shackles, do not allow controlled but partial movement. Once the handcuff or shackle has been unlocked, the person's arms or legs are completely unrestrained and he can run, lash out at those around him or reach for and perhaps obtain a weapon. The escorting officers, guards or medical attendants can restrain the person's released arms or legs only by physically holding the arms or legs, which puts them in danger and which has the potential to cause physical injury to the prisoner or patient. Further, depending on the relative size and strength of the person and the escort, the person may well be able to overpower the escort once his arms and legs are freed.

Further, keeping the person restrained in the conventional handcuffs, shackles, etc., is often impractical or injurious, particularly where the restraint must be maintained for a prolonged period of time or where the person must be moved about extensively.

An experimental restraint belt was developed as an earlier part of the project which led to the present invention and was described in Law Enforcement Quarterly (February–April, 1993), pp. 25–26. This belt was of limited capability, since it did not have any facility for continuous control of a prisoner's hands while the prisoner was fingerprinted, had blood drawn, etc., nor did it permit rapid control if a prisoner attempted to bolt or attack. Its only functions were to lock a prisoners hands at his sides and permit his transport by officers. Thus, while it served an initial limited purpose and a prototype sample was considered and tested by a major metropolitan police department, it was found to be significantly limited in application and was never put into service. Clearly substantially more capacity for various restraint and control functions, and particularly the need for rapid and absolute control of a prisoner or other person to be restrained, is needed for a truly versatile device.

SUMMARY OF THE INVENTION

The present invention is advantageously a restraint device which serves to secure a person's arms, and optionally also legs, while yet providing for a limited amount of movement of his arms or legs, but only under complete control of an escorting person such as a police officer or guard. The controlling means are operable by the escorting officer or guard from a position which allows the escort to control the person while preventing the person from attacking or inflicting harm on the escort or others in the immediate vicinity. Locks on the device prevent the person from releasing himself from the restraint device.

In a preferred embodiment, the invention herein is a restraint device to limit the movements of a person, which comprises an elongated belt having a first end with a hasp adjacent thereto, an opposite second end with a belt buckle adjacent thereto, the ends being releasably connectible by interconnection of the hasp and the belt buckle to secure the belt around the person's waist; a pair of arm restraints each comprising an elongated tether and with a releasable arm clamp at one end thereof for securement to a respective arm of the person and restriction of the person's movement of the arm; each the arm restraint being independently attached to the belt by a tether buckle on the belt, the tether being securable to the tether buckle at a plurality of positions to provide variable distance between the belt and the arm clamp; and the buckles and the arm clamps all having lock means to control the releasability of the buckles and the arm clamps. A restraint device as in claim 1 wherein length of the belt between the first and second ends when connected by the belt buckle is adjustable, such that different waist sizes of persons can be accommodated.

The restraint device may also include leg restraint means, the leg restraint means comprising an elongated tether secured at one end to the belt and having a loop at an opposite end thereof for securement to at least one leg of the person, the leg restraint means also comprising lock means to control the length of the tether and thereby restrict the person's movement of the leg.

When the belt is positioned about the person's waist and the arm clamps are secured to the person's arms, all the buckles are locked and inoperable by the person, even where it is possible for the person to reach and make contact with a buckle. The same is true when the leg restraint is used. Preferably all of the buckle locks are operable by a single type of key, such as a handcuff key.

Other aspects of the invention include a belt buckle comprising a housing, a releasably lockable latch closing the housing, a pawl moveably attached to the latch, and engaging means in the housing for attaching the buckle to the belt, such that when the hasp is inserted into the buckle the buckle and the hasp are interconnected by engagement of the pawl into a recess in the hasp, and the interconnection can be released only by unlocking the lockable latch.

Yet other aspects of the invention include a tether buckle comprising a housing, a movable pawl within the housing, and a lockable cam engaging the pawl, such that when the tether is extended within the housing it is disposed in engagement with the pawl and secure against extension out of the housing by the pawl, and the cam can be unlocked to urge the pawl away from the engagement with the tether and permit the extension movement of the tether.

The present belt will therefore be profitably used by law enforcement agencies, by prisons or jails, by park or forest rangers or wardens, in courts by bailiffs and by other similar agencies. They will also find use in medical and psychiatric hospitals and facilities, particularly in emergency facilities where restraint of violent persons for appropriate emergency medical treatment may be necessary.

DETAILED DESCRIPTION AND PREFERRED EMBODIMENTS

Figures 1, 2:
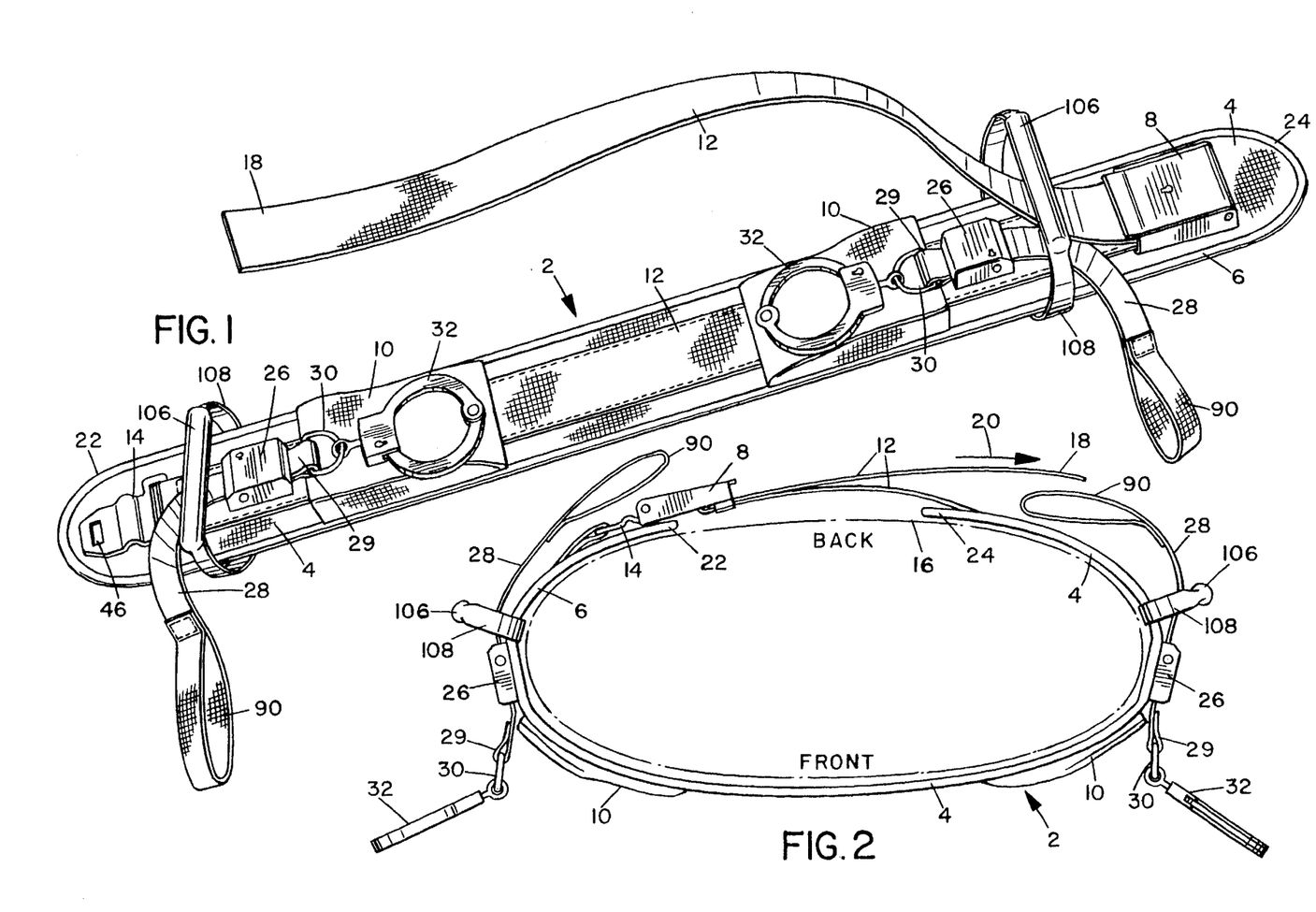
FIG. 1 is a perspective view of the restraint belt of this invention.
FIG. 2 is a top view of the belt fastened as in use.
Figure 3:
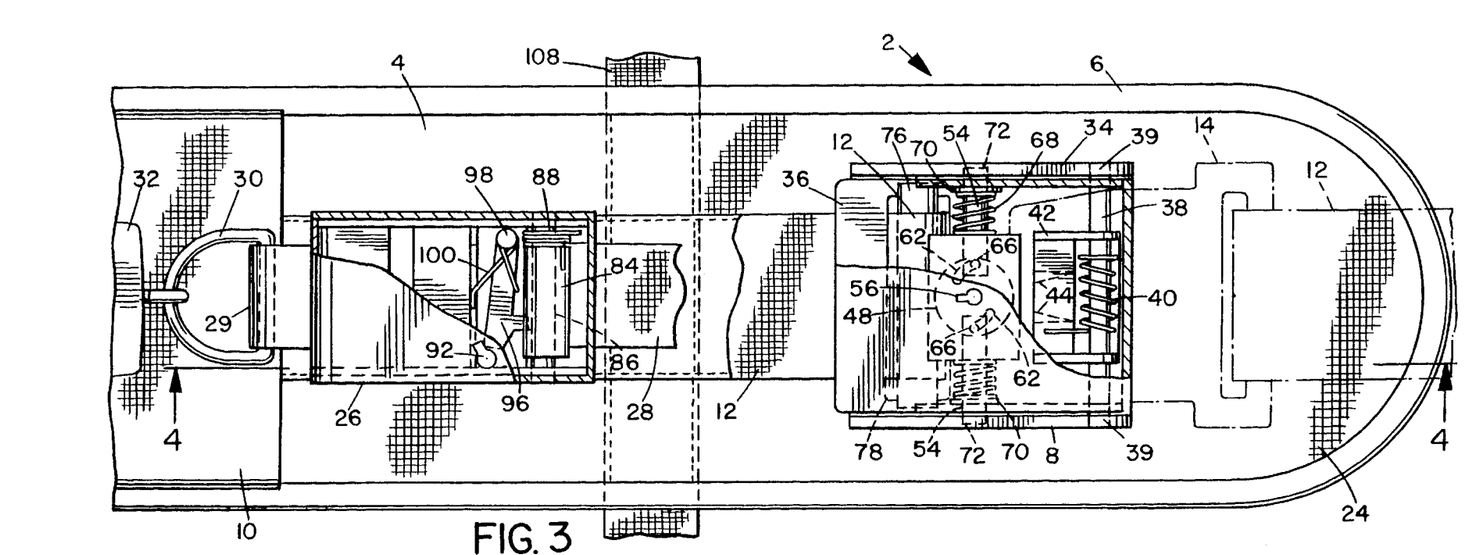
FIG. 3 is an enlarged plan view of the buckle end of the belt.

The present invention is best understood by reference to the drawings. FIG. 1 shows an overall view of the restraint belt 2 of the present invention in an overall view. The belt 2 has as its base an elongated strip 4 of strong flexible belt material. Typical suitable types of material will be described below. The overall structure of the belting material is such that there is no elasticity in the belt. The strip 4 is preferably strengthened by having sewn to it a strong continuous edge piece 6 which resists fraying and cutting of the edges, and also reinforces the strip 4 against stretching.

Positioned at one end of the belt 2 but not attached to the strip 4 is locking belt buckle 8. Also attached to strip 4 are pockets 10, whose function will described below. Lying along the strip 4 and secured thereto normally by sewing with stitching 11 is belt length adjusting strap 12. In additional to the stitching 11 the strap 12 may also be secured by rivets 104, both those which secure the buckles described below and also rivets which may be positioned elsewhere along the length of the strap 12. Strap 12 is looped through buckle 8 at one of its ends and attached to hasp 14 at its other end. Hasp 14 is configured to fit into buckle 8 and be latched therein, in a manner analogous to latching of an automobile or airplane seat belt.

Figure 12:
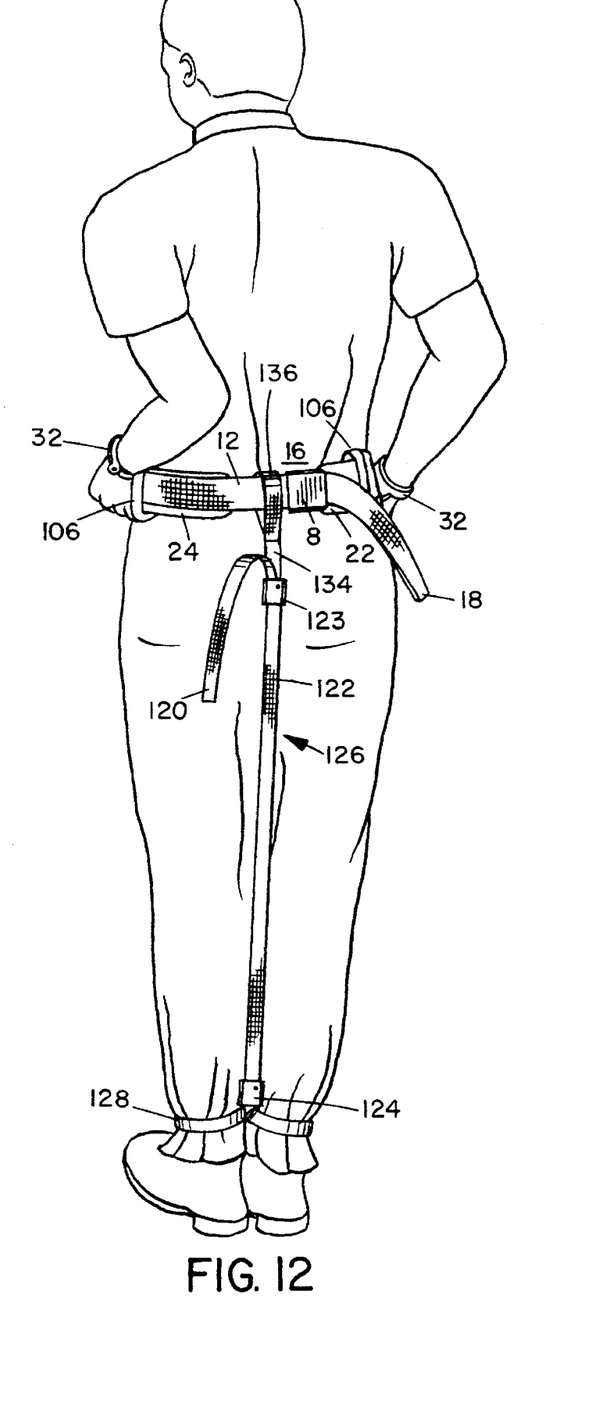
FIG. 12 illustrates the restraint device, including the leg restraint member, as used to restrain a person.

Belt 2 is secured around the waist of the restrained person in a manner illustrated in FIGS. 2 and 12. The person's waist 16 in cross section is schematically indicated by a phantom line, with the person's front and back labeled to indicate the orientation of the belt 2 with respect to the person. The belt 2 in its open position (FIG. 1) is first looped around the person's waist 16 with the open portion between ends 22 and 24 positioned behind the person's back. The buckle 8 is then extended outwardly past end 24 with strap 12 moving through it until it meets and connects with hasp 14. Once the hasp 14 is latched into the buckle 8, the free end 18 of strap 12 is pulled, quickly retracting buckle 8 and hasp 14 back toward the belt strip 4 until the entire belt 2 is securely fitted around the prisoner's waist 16. Commonly for prisoners of average build, the ends 22 and 24 of the strip 4 will overlap when the belt 2 is securely drawn tight around the person's waist. The buckle 8 then locks the strap 12 against further movement by a mechanism to be described below.

Also attached to belt 2 are a pair of handcuff buckles 26. Through each buckle 26 is threaded a tether strap 28, one end of which is formed into a loop 29 through holding a ring 30 to which is attached a handcuff :32. The buckles 26 are placed on the belt 2 such that when the belt 2 is drawn tight around the person's waist 16, the buckles 26 are positioned to the person's sides, usually directly above his hips. When the tether straps 28 are fully retracted through buckles 26, the handcuffs 32, which are attached to the person's wrists, thus secure his wrists at a position very close to his sides, so that he cannot clasp his hands together, move them away from being pinioned close to his waist and hips, or operate any of the buckles.

The minimum distance between the two buckles 26 will be sufficiently great that when the handcuffs 32 are clamped on the person's wrists and straps 28 are fully retracted, even a small waisted prisoner cannot clasp his pinioned hands together. The overall length of the strip portion 4 of the belt 2 and the strap 12 will be such that the waist sizes of most adults can be accommodated, although there will be varying degrees of separation or overlap of ends 22 and 24 depending on the person's waist size. Smaller length belts can be manufactured to accommodate youths or adults of particularly small stature. Similarly, belts can be made in larger sizes to accommodate particularly large or obese individuals.

Each of the buckles 8 and 26 is respectively designed to lock automatically against movement of strap 12, preventing extension of the belt 2, or strap 28, preventing extension of handcuff 32, but to freely operate to tighten the belt 2 or shorten the distance of the handcuff 32 from the belt 2. Only by insertion of a key can a buckle 8 or 26 be released to allow extension of the belt 2 or handcuff 32. The buckle structures to accomplish this are illustrated in FIGS. 3–9.

Figure 4:
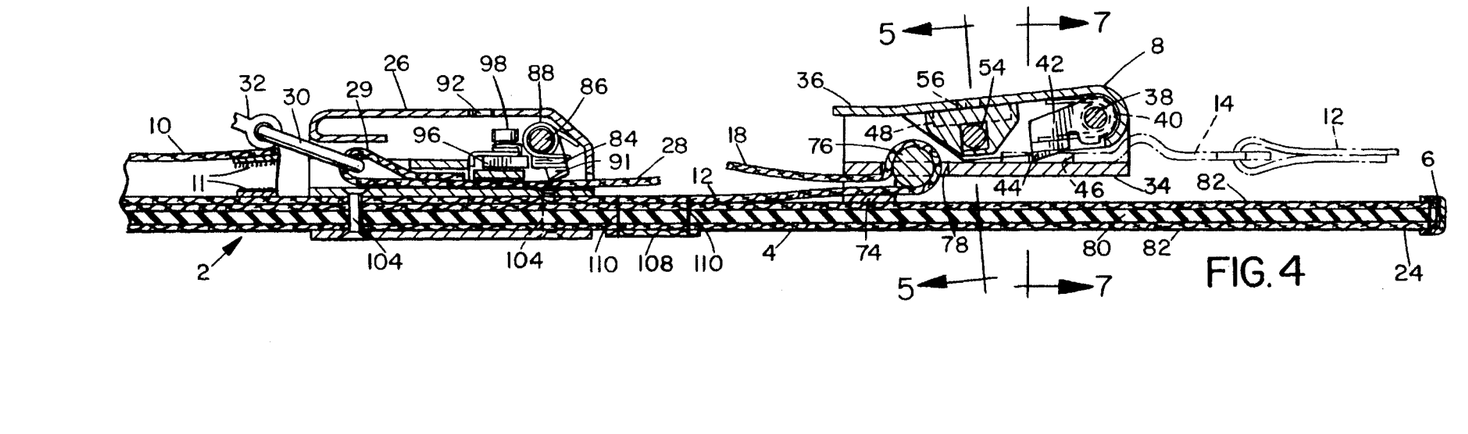
FIG. 4 is a sectional view taken on line 4—4 of FIG. 3.

Considering first belt buckle 8, it will be seen that buckle 8 has a casing 34 to which is pivotally attached a latch 36, which pivots on axle 38 which in turn is mounted in holes or recesses 39 in casing 34. A torsion spring 40 contacts both latch 36 and pivoting pawl 42 whose beveled tip 44 fits into hole 46 in hasp 14 when hasp 14 is inserted into the buckle 8. The torsion spring 40 has a limited stiffness which allows the hasp 14 to move the pawl tip 44 upward as the hasp 14 is inserted into the buckle 8 but which is still sufficient to force the pawl 42 downward to drive tip 44 down into the hole 46 as the hole and tip come into alignment and to maintain tip 44 in hole 46 until the latch 36 is lifted. Because the pawl 42 pivots, hasp 14 can be inserted and locked into buckle 8 without the need for use of key 58 or lifting or unlocking of latch 36.

When closed, latch 36 is held in a locked position by a cam and rod structure. The cam 48 is mounted in a housing 50 which includes a recess 52 for laterally moving rods 54. There is a keyhole 56 in the latch 36 for entry of a key 58 which also fits into a corresponding hole 60 in cam 48, such that rotation of the key 58 also rotates the cam 48. As the cam 48 rotates, it moves grooves 62 formed in the cam 48 and into which are fitted cam followers 64. Cam followers 64 are mounted in holes 66 in rods 54 such that rotation of key 58 turning cam 48 causes cam followers 66 moving in grooves 62 to retract rods 54 into the inside of casing 34, so that latch 36 can be lifted. When the key 58 is rotated back to its original position, compression springs 68 expand and push against flanges 70 on rods 54, while cam followers 64 move in grooves 62 and the rods 54 are extended outwardly. The ends 55 of rods 54 are beveled so that the latch 36 can be closed and locked, with rods 54 being urged into blind holes 72 in housing 34 by springs 68 without the need for use of key 58, thus securing latch 36 from being lifted and hasp 14 being freed until a subsequent use of key 58.

Strap 12 is threaded through an anti-slip bracket 74 and loops around a free roller 76 which is positioned in an opening 78 in the bottom of housing 34, with the free end 18 of strap 12 being rethreaded through the bracket 74 and out of the buckle 8 to a position where it can be manipulated by hand. When the free portion of strap 12 is fed toward the buckle 8 slack is created in the strap 12 as it moves around roller 76 (clockwise in the views show in FIGS. 4 and 6), and allows the buckle 8 to be moved freely outwardly to engage fixed hasp 14. Pulling on the free end 18 in the opposite direction causes retraction of the buckle 8 until the belt 2 is cinched securely around the person's waist. Bracket 74 forces the strap 12 to move only in a straight path both toward and away from roller 76, which prevents the strap 12 from slipping after it is pulled tight and allowing the belt 2 to become loose or slack.

A preferred structure for the strip 4 of belt 2 is also illustrated in FIG. 4. A core of a relatively dense elastomeric or foam material 80 is encased on both sides by woven materials 82 and the three layers are stitched and/or riveted securely together. The presence of the elastomeric or foam material 80 provides a limited degree of "give" to the thickness of the belt. Therefore, even though there is no elasticity in the width or length of the belt 2, there is a small amount of resiliency across the thickness of the belt so that the edges 6 of the belt 2 do not tend to cut into the person's skin.

Also illustrated in the Figures is the mechanism which permits the handcuff buckles or latches 26 to allow for positive control of the amount of extension or freedom allowed to the person's hands and arms, while still retaining his wrists secured in the handcuffs 32. Within the latch housing 26 is a moveable pawl 84 which is mounted on a rod 86 around which is coiled torsion spring 88. The pawl is positioned at an angle to tether strip 28 and has a leading edge 91 beveled so that when engaged it resists any movement of the tether strap 28 in the direction which would permit outward movement of the strap 28 and handcuff 32. However, the angled position of pawl 84 does not resist movement of strap 28 in the other direction when the free end 90 of the strap 28 is pulled to withdraw the loop 29 and handcuff 32 back securely adjacent to the latch 26, again pinioning the person's hand at his side. A keyhole 92 is formed in the top of latch 26 through which a key 94 can be inserted to engage cam 96 which rotates on pivot 98. As the key 94 is turned, it pivots the cam 96 toward the pawl 84, causing the pawl 84 to rotate around the shaft 86 and be pushed away from engagement with the strap 28, so that the handcuff 32 can be pulled out and extended away from the latch 26. When the key is removed, a torsion spring 100 retracts the cam 96 and allows the pawl 84 to drop down under the influence of spring 88 and once again engage the tether strap 28. A stop 102 prevents the cam 96 from moving out of alignment near the cam 84. Thus, by use of the key 94 the handcuff 32 can be extended to permit some limited movement of the person's hand, but a quick pull on the free end 90 of the tether strap 28 will cause the handcuffed hand (and the prisoner's wrist and arm), to be quickly and securely drawn back against the prisoner's side. Thus a person's arm can be freed sufficiently to allow him to be fingerprinted, receive medication or give a blood or urine sample, write something or hold belongings or papers, but the escorting officer, guard, etc. maintains sufficient control through use of strap 26 to be able to quickly pinion the person's arm and hand if the person attempt to use his freed hand in an impermissible manner. The free ends 90 of the straps 28 may conveniently be formed as closed loops as shown to provide the escort with a more secure grip on the straps 28 and ability to respond quickly and effectively if the person being restrained makes a sudden movement. Although not shown, the ends 18 and 120 of straps 12 and 122 respectively may also be formed as loops if desired.

Each of the buckles 8, 26, 112 and 124 may be operable with different keys. This may be an advantage where certain custodial persons need to work with a restrained person for limited purposes, but are not authorized to release the restrained person from all restraints. Such would be the case, for instance, where a laboratory technician needed access to a restrained person's arm to obtain a blood sample, but was not otherwise authorized to release the person from the remainder of the restraints. In this situation the buckles would be structures so that the technician's key would fit and operate only the arm restraint handcuff buckles 26. In most cases, however, it is preferred that all buckles 8, 26, 112 and 124 be operable with a single type and cut of key (keys illustrated as 58 and 94 thus actually being equivalent keys), so that a single officer or medical attendant could exercise full control over the amount of restraint. Commonly, especially where the device is used by law enforcement personnel, the single key will be a handcuff key, since normally all officers in a law enforcement organization carry identical handcuff keys. This permits the belt to be operated by any officer with a handcuff key, and separate or special keys are unnecessary. This is particularly convenient when a person is put into the belt by officers at an arrest location and, after the person is transported to a detention or medical facility, different officers at that facility can unlock the buckles as needed.

The handcuff buckles 26 are secured to the strip 4 of the belt 2 by rivets 104. Also a pocket 10 is positioned on belt 2 in front of each buckle 26 for convenient storage of the handcuff 32 when the belt is not in use. A pair of opposed restriction strips 11 at the entrance to pocket 10 help to retrain the handcuffs 32 within the pocket 10 until they are needed.

Also preferably attached to the belt 2 is at least one and preferably a pair of handles 106 which are secured to belt strap 108 which in turn is securely stitched and/or riveted to the strip 4 as indicated at 110.

Figure 11:
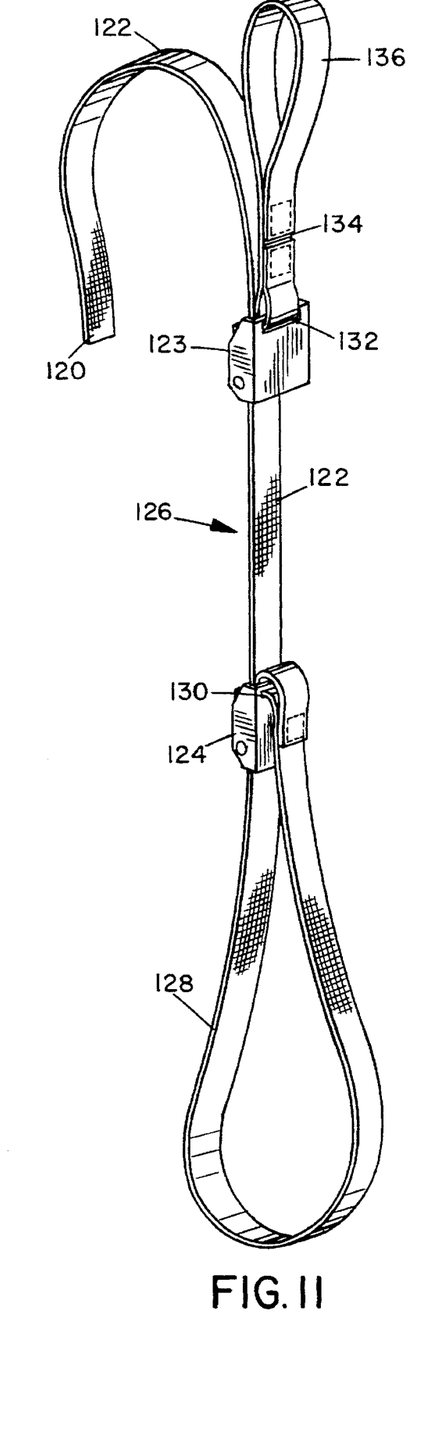
FIG. 11 is a perspective view of a leg restraint member for use as part of the present invention.

Also preferably included in the invention is leg tether 126 shown in FIGS. 11 and 12. This is used to secure one or both of the person's legs and either prevent or severely restrict his ability to walk or run. The leg tether 126 consists of strap 122, which runs from free end 120 through buckles 123 and 124, forming a loop 128 which returns to and is secured to buckle 124 through slot 130. Buckles 123 and 124 are mechanically the same as buckles 26, including the locking mechanisms, except for the provision of slots 130 and 132. A separate strap 134 of fixed, relatively short, length is secured to buckle 123 through slot 132 and has at its other end a fixed loop 136. When the leg tether 124 is to be used, loop 136 is slid over buckle 8 and strap 12 so that when buckle 8 and hasp 14 are connected, loop 136 is secured to belt 2 as shown in FIG. 12. The adjustable loop 128 is then placed about one or both of the person's legs, usually near the ankles, and drawn tight by pulling strap 122 through buckle 124. The overall length of the tether 124 is then adjusted by pulling strap 122 through buckle 123 until the desired tether length is obtained. By attaching loop 128 to only one of the person's legs, and then drawing the length of the tether 124 to a length which allows the person only to have his toes on that tethered leg touch the ground, the person will be capable of walking, albeit in a halting, hobbled fashion, but cannot run. If full restraint is desired, both legs can be restrained by loop 128, and the length of the tether 122 may sufficiently short that the person's legs are drawn up behind him, so that he can only lie down or sit.

Figures 5, 6, 7, 8, 9, 10:
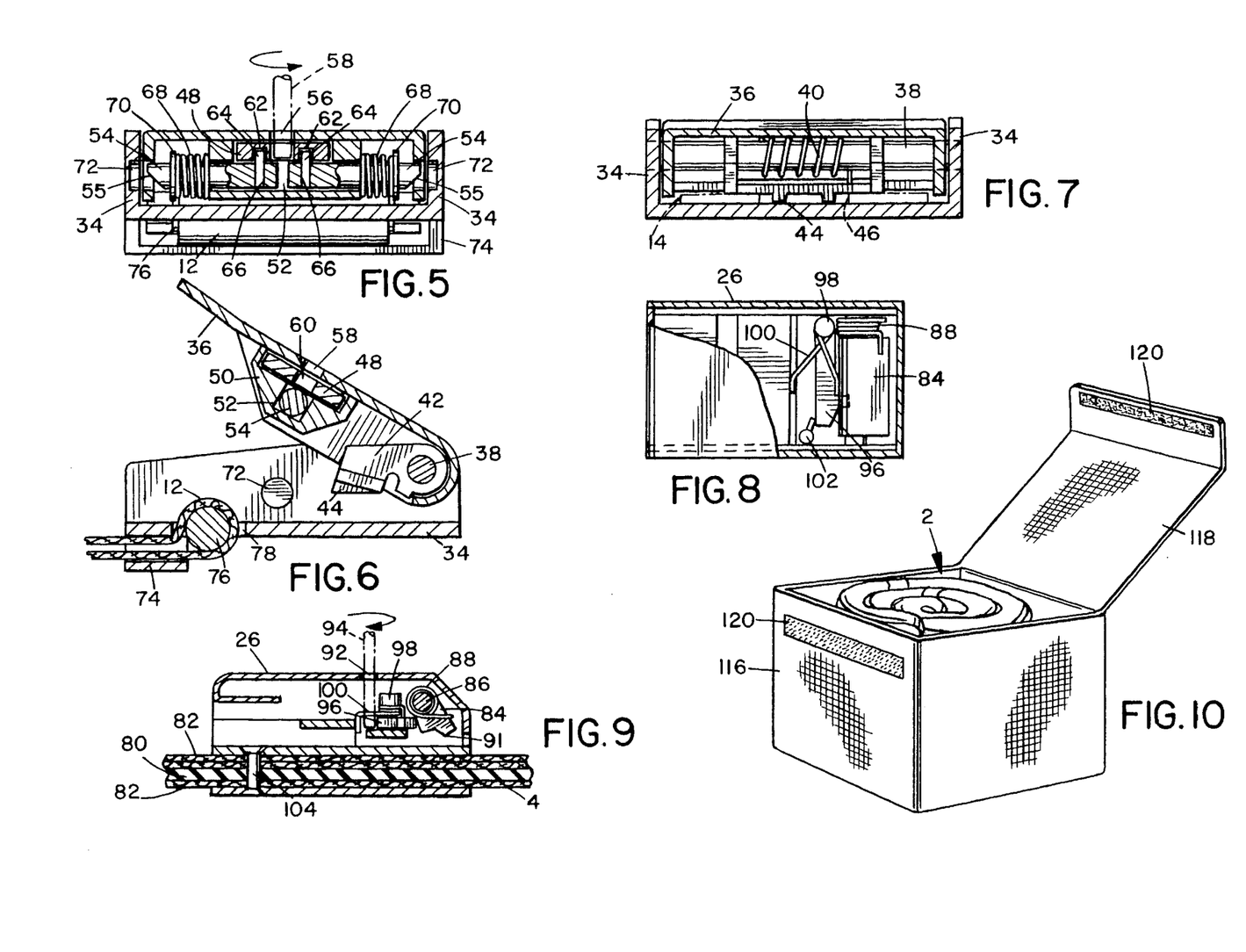
FIG. 5 is an enlarged sectional view taken on line 5—5 of FIG. 4.
FIG. 6 is an enlarged view similar to a portion of FIG. 4, with the buckle shown unlocked and opened.
FIG. 7 is an enlarged sectional view taken on line 7—7 of FIG. 4.
FIG. 8 is a view similar to a portion of FIG. 3, with the handcuff latch shown unlocked.
FIG. 9 is a view similar to a portion of FIG. 4, with the handcuff latch shown unlocked.
FIG. 10 illustrates the belt stored in a container.

For convenience, when not in use the belt 2 (including the leg tether 122) can be coiled up and stored in a storage container 116 which has a lid 118 which can be secured in a closed position as by interconnecting fabric strips 120, such as those available under the trade name "Velcro." Such a container can easily be stored in a location convenient for police, hospital personnel, etc., such as by being carried in a police patrol car trunk or kept in a hospital emergency room storage cabinet.

Also, it is preferred practice to have all buckles and straps "reset" after each use and before storage, with the straps pushed back through the buckles for most of their length, so that the straps and buckles are as "open" as possible, while maintaining short lengths of straps for the officers, attendants, etc. to pull on while restraining the person. This permits the device to be used initially to restrain the person as quickly as possible, since an officer needs only to pull quickly on a strap to secure it, and does not first need to unlock a buckle to loosen and put slack into it.

The various straps and buckles will be designed with just enough freedom of action when slack to permit the straps to be operated very quickly (substantially instantly) by the officer, guard, attendant, etc. subduing or escorting the restrained person, so that the escort can immediately act to prevent the restrained person from making or completing any sudden unauthorized movement.

The following descriptions will illustrate to those skilled in the art the wide variety of ways in which the restraint belt 2 of this invention can be used. Consider first the situation where a criminal has been taken into custody by arresting officers. The officers first handcuff the person with his hands behind his back, using conventional handcuffs. (The device of the present invention is not normally appropriate for use as part of the initial capture and securing of the criminal.) The officers now wish to move the prisoner to a patrol car or other vehicle for transport to a detention facility. In the past the common practice has been simply to place the prisoner, with his hands still handcuffed behind his back, in the back seat of the patrol car with no further restraints. This allows the person to still manage quite a bit of voluntary movement. It also results in much involuntary movement caused by the motion of the patrol car, and the prisoner can be thrown from side to side and possibly injured. Further, the ability to move voluntarily may allow the prisoner to work out of the handcuff restraints, unfortunately not an entirely uncommon occurrence. The prisoner is then free to attack the officer driving the car or to try to seize the officer's weapon. It is also possible in some vehicles for the prisoner to unlatch a vehicle door and flee from the vehicle, particularly since handcuffs of course do not secure the prisoner's legs in any manner. Finally, prolonged riding by the prisoner in a position with his hands handcuffed behind his back can cause injury to the prisoner's arms, shoulders, back or neck.

With the present invention however, the arresting officers, having initially secured the prisoner's hands behind his back with conventional handcuffs, can then take the belt 2 and secure it around the prisoner's waist by connecting the hasp 14 and buckle 8 and pulling the strap 12. The belt 2 will be positioned such that the buckle 8 will be at the middle of the prisoner's back, essentially adjacent the small of his back, as shown in FIG. 12. With the device in its "reset" position, each of the handcuffs 32 can be secured to the prisoner's wrists, while the prisoner's wrists are still handcuffed behind his back with the officer's conventional handcuffs, and the arresting officer can then immediately pull on the free end 90 of each of the tether straps 28 while the conventional handcuffs are being released, so that the prisoner's hands are drawn forward from behind his back and secured at his sides adjacent his hips. It will be recognized that at no time are the prisoner's hands or arms freed from restraint, since the handcuffs 32 are secured around his wrists and the straps 28 at least partially drawn tight before the conventional handcuffs are released. If it is desired to secure the prisoner's legs, the leg tether 122 can at the same time be secured to the prisoner's ankles as described above, with the appropriate amount of length to determine whether or not the prisoner will be allowed to walk (albeit with a hobbled gait).

Thereafter, the prisoner can be moved to the patrol car, with the arresting officer using one or both of the handles 106 to guide the prisoner and to steady him (in the event that through injury, intoxication or similar condition his walk is unsteady). Once the prisoner is seated in the patrol car conventional seat belts of the patrol car can be looped through the two handles 106, buckled and then pulled tight, such that the prisoner is restrained in position sitting on the seat of the patrol car and can neither move of his own volition or be thrown from side to side by the motion of the patrol car. Further, since the prisoner's hands are secured at his sides, he cannot reach the seat belt buckle to free himself from restraint to the seat, nor can he reach toward the officer driving the vehicle. If he is secured in the middle of the back seat of a patrol car, he will also be unable to reach any latch on the car door.

The handles 106 can also be used to lift and carry a prisoner whose legs are restrained by tether 122 or who is uncooperative about walking on his own or who, perhaps through intoxication or the like, is unable to walk. This feature is particularly useful when taking civil disobedience demonstrators into custody, since a demonstrator who refuses to walk or otherwise cooperate with officers can be secured into the belt 2 and then carried from the location (as to a vehicle) with minimal chance of injury either to the demonstrator or to the officers.

Once the prisoner is delivered to the station house or other detention facility, he can remain secured in the belt 2 while undergoing the normal booking procedures. When it is time to fingerprint the prisoner, each of the arm restraints can be extended individually, so that only one of the prisoner's arms has limited freedom at a time. The handcuff 32 remains attached to the prisoner's free wrist, so that his arm can be extended to conduct fingerprinting, write when appropriate, hold belongings or papers or otherwise use one arm at a time. Should, however, the prisoner make any untoward moves the escorting officer can simply pull on the free end 90 of the tether strap 28 and the prisoner's free hand is immediately drawn back to securement at his waist. When the fingerprinting or other activity with one hand is completed, the strap 28 can be drawn back in the same manner as described, but normally in a less abrupt manner, and when the one arm is back secured by the prisoner's side, then his other arm can be partially released (with the handcuff 32 still attached) and the fingerprints of the other hand taken or other use of the prisoner's other arm conducted.

Another example of the need to free one arm at a time while still keeping the free arm under control might be where the person's blood samples need to be taken or where medication needs to be injected into him. It is also possible to have the restraint belt remain in position while the prisoner receives medical treatment, to keep him from attacking medical personnel with his free hands. A similar use occurs when a prisoner needs to be transported between one facility and another, such as when a prisoner is being brought from jail to a courtroom for arraignment, trial or other proceeding, or transferred between detention facilities. The prisoner can be fitted with the belt while still in his cell and his arms restrained either completely or with a small degree of freedom, so that he can carry belongings or court papers. When the prisoner is placed in the transporting vehicle, he can be secured to his seat as described above. It is convenient for all prisoners in the vehicle to be wearing a restraint belt of this invention. Thus, for instance, where a prison bus is used to transport a number of prisoners simultaneously, either to another facility or to a court, each of the prisoners can be individually fitted with a belt of the present invention and secured to a separate seat in the prison vehicle. Thus a minimum number of escorts or guards will be needed for the vehicle, since on loading or unloading the prisoners from the vehicle, each prisoner can be dealt with individually while the other prisoners remain secured to their seats with their arms pinioned by their waists. The escorting officers then are in little danger of having any group of prisoners try to overwhelm them and escape, since only one prisoner at a time will be allowed to move from his seat and enter or leave the vehicle.

Further, since the leg tether, if in use, can be separately controlled and released, a prisoner's legs can be restrained or freed independently of his arms. Thus a prisoner's legs can be freed for him to walk while, inside a detention facility although his arms are still restrained, or conversely, his arms can be freed for taking blood or handwriting samples, etc., while his legs remain restrained against his possible attempt at flight.

The belt of the present invention can be used for many types of persons where maximum but controllable restraint is needed, and most advantageously, where the degrees of restraint of different portions of a person's body are to be individually controllable. While the most common usage will be by law enforcement personnel with uncooperative, violent or potentially dangerous criminals, a belt of this type may also be used by law enforcement or medical personnel with mentally ill persons whose violent movements might be a danger to themselves or to others, with persons who are acting violently because of drug or alcohol ingestion, or to secure persons who, while perhaps not acting criminally, are acting irrationally. Thus, the belt of this invention may be used to restrain participants who have been engaging in brawling, domestic violence, civil disobedience or the like. The present belt will also be profitably used by law enforcement agency, prison or jail personnel; by park or forest rangers or wardens; in courts by bailiffs and by other similar agencies. They will also find use in medical and psychiatric hospitals and facilities, particularly in emergency facilities where restraint of violent persons for appropriate emergency medical treatment may be necessary.

The belt 2 and its components may be made of conventional materials. Some of the types of straps, webbing, foam or elastomer for the belts themselves have been described above and many other useful materials will come readily to mind. Typical are the many types of woven fabrics used for other belting products such as vehicle seat belts, ammunition belts, military belts and the like. The handcuffs 32 and buckles will commonly be made of metal or very strong plastics. Steel, aluminum or some of the engineering plastics would be quite suitable. If some cases, as with mental patients, it may be desirable to cover the components of each handcuff with a padded material such as cloth or rubber to prevent the patient from injury. The handles 106 are preferably made of a hard wood or rubber or strong plastic, either directly exposed or disposed as a solid core around which a fabric material is placed.

It will be evident that there are many other embodiments of the present invention which, while not expressly described above, are clearly within the scope and spirit of the invention. The above description is therefore intended to be exemplary only, and the scope of the invention is to be determined solely by the appended claims.

We claim:

1. A restraint device to limit the movements of a person, which comprises:

an elongated belt having a first end with a hasp adjacent thereto, an opposite second end with a belt buckle adjacent thereto, said ends being releasably connectible by interconnection of said hasp and said belt buckle to secure said belt around said person's waist;

a pair of arm restraints each comprising an elongated arm tether and with a releasable arm clamp at one end thereof for securement to a respective arm of said person and restriction of said person's movement of said arm;

each said arm restraint being independently attached to said belt by a tether buckle on said belt, said arm tether being securable to said tether buckle at a plurality of positions to provide variable distance between said belt and said arm clamp; and said buckles and said arm clamps all having lock means to control the releasability of said buckles and said arm clamps.

2. A restraint device as in claim 1 wherein length of said belt between said first and second ends when connected by said belt buckle is adjustable, such that different waist sizes of persons can be accommodated.

3. A restraint device as in claim 1 wherein when said belt is positioned about said person's waist and said arm clamps are secured to said person's arms, all said lock means are inoperable by said person.

4. A restraint device as in claim 1 wherein said lock means are operated independently but by a single key.

5. A restraint device as in claim 4 wherein said single key is a handcuff key.

6. A restraint device as in claim 1 further comprising leg restraint means, said leg restraint means comprising an elongated tether secured at one end to said belt and having a loop at an opposite end thereof for securement to at least one leg of said person, said leg restraint means also comprising lock means to control the length of said tether and thereby restrict said person's movement of said leg.

7. A restraint device as in claim 6 wherein said loop may restrict movement of one or both of said legs.

8. A restraint device as in claim 6 wherein said elongated tether is adjustable in length such that said person's legs may be restrained such that said person is incapable of any walking or such that limited walking is possible.

9. A restraint device as in claim 6 wherein when said belt is positioned about said person's waist and said arm and leg restraint means are secured to said person's arms and legs respectively, all said lock means are inoperable by said person.

10. A restraint device as in claim 6 wherein said lock means are operated independently but by a single key.

11. A restraint device as in claim 10 wherein said single key is a handcuff key.

12. A restraint device as in claim 1 wherein said belt buckle is disposed such that when said belt is secured around said person's waist said belt buckle is adjacent said person's back.

13. A restraint device as in claim 1 wherein each said arm tether buckle is disposed such that when said belt is secured around said person's waist said tether buckle is adjacent a lateral side of said person respectively.

14. A restraint device as in claim 1 further comprising at least one handle attached to said belt.

15. A restraint device as in claim 1 wherein said belt buckle comprises a housing, a releasably lockable latch closing said housing, a pawl moveably attached to said latch, and engaging means in said housing for attaching said buckle to said belt, such that when said hasp is inserted into said buckle said buckle and said hasp are interconnected by engagement of said pawl into a recess in said hasp, and said interconnection can be released only by unlocking said lockable latch.

16. A restraint device as in claim 15 wherein said engaging means comprises a roller at least partially within said housing around which is secured a flexible elongated strip attached to said belt.

17. A restraint device as in claim 16 wherein said strip can be moved around said roller to permit movement of said buckle along the length of said strip.

18. A restraint device as in claim 17 further comprising means to cause segments of said strip located adjacent to said roller to be oriented in the same direction, such that a segment of said strip in contact with said roller cannot slip on said roller.

19. A restraint device as in claim 15 wherein said lockable latch is operated by a key.

20. A restraint device as in claim 19 wherein said single key is a handcuff key.

21. A restraint device as in claim 1 wherein said tether buckle comprises a housing, a movable pawl within said housing, and a lockable cam engaging said pawl, such that when said tether is extended within said housing it is disposed in engagement with said pawl and secure against extension out of said housing by said pawl, and said cam can be unlocked to urge said pawl away from said engagement with said tether and permit said extension movement of said tether.

22. A restraint device as in claim 21 wherein said pawl is urged by a spring into said engagement with said tether and movement of said cam is opposite the movement urged by said spring.

23. A restraint device as in claim 21 wherein said lockable cam is operated by a key.

24. A lockable buckle in combination with a separate unlocking means for attachment to a belt, said belt also having a hasp at one end thereof, said buckle comprising a housing, a releasable latch closing said housing, a lock incorporated in said latch and locking when said latch is closed and thereafter being unlockable only by interaction with said separate unlocking member, a pawl moveably attached to said latch, and engaging means enclosed within said housing for securing said buckle to said belt, such that when said hasp is inserted into said buckle and said latch is closed and said lock locked, said buckle and said hasp are interconnected by engagement of said pawl into a recess in said hasp, said interconnection can be released only by unlocking said lock with said unlocking member and engagement of said belt at said engaging means is inaccessible to a wearer of said belt.

25. A buckle as in claim 24 wherein said engaging means comprises a roller within said housing around which is secured a flexible elongated strip attached to said belt.

26. A buckle as in claim 25 wherein said strip can be moved around said roller to permit movement of said buckle along the length of said strip.

27. A buckle as in claim 26 further comprising means to cause segments of said strip located adjacent to said roller to be oriented in the same direction, such that a segment of said strip in contact with said roller cannot slip on said roller.

28. A buckle as in claim 24 wherein said unlocking member comprises a key.

29. A restraint device as in claim 28 wherein said key is a handcuff key.

30. A lockable buckle in combination with a separate unlocking means for attachment to a tether in the form of a strap and comprising a housing, a movable pawl within said housing, and a cam engaging said pawl, a lock interacting with said cam and locking when said buckle is closed and thereafter being unlockable only by interaction with said separate unlocking member, such that when said tether is extended within said housing it is disposed in engagement with said pawl and secure against extension out of said housing by said pawl, said pawl and a portion of said tether in engagement therewith are inaccessible to a wearer of said belt, and said lock interacting with said cam can be unlocked only with said unlocking member to urge said pawl away from said engagement with said tether and permit said extension movement of said tether.

31. A buckle as in claim 30 wherein said pawl is urged by a spring into said engagement with said tether and movement of said cam is opposite the movement urged by said spring.

32. A buckle as in claim 30 wherein said unlocking member comprises a key.

33. A restraint device as in claim 32 wherein said key is a handcuff key.

* * * * *